United States Patent
Cauchard et al.

(10) Patent No.: US 8,293,287 B2
(45) Date of Patent: Oct. 23, 2012

(54) **USE OF A *BRASSOCATTLEYA MARCELLA* KOSS ORCHID EXTRACT AS AN ACTIVE AGENT TO PREVENT OR DELAY THE APPEARANCE OF SIGNS OF CUTANEOUS AGING**

(75) Inventors: Jean Hubert Cauchard, Orleans (FR); Jean-Christophe Archambault, Meung S/Loire (FR); Kristell Lazou, Orleans (FR); Frederic Bonte, Orleans (FR)

(73) Assignee: L V M H Recherche, Saint Jean de Braye (FR)

( * ) Notice: Subject to any disclaimer, the term of this patent is extended or adjusted under 35 U.S.C. 154(b) by 0 days.

(21) Appl. No.: 12/382,250

(22) Filed: Mar. 11, 2009

(65) Prior Publication Data

US 2009/0258093 A1 Oct. 15, 2009

(30) Foreign Application Priority Data

Mar. 13, 2008 (FR) ..................... 08 51640

(51) Int. Cl.
*A61K 36/00* (2006.01)
(52) U.S. Cl. ........................................ 424/725
(58) Field of Classification Search ............... None
See application file for complete search history.

(56) References Cited

U.S. PATENT DOCUMENTS

2008/0020077 A1 1/2008 Leclere

FOREIGN PATENT DOCUMENTS

| FR | 2 784 027 | 7/2001 |
|----|-----------|--------|
| JP | 2004-067549 | 4/2004 |
| WO | WO 2004/093839 | 11/2004 |
| WO | WO 2006/000689 A1 | 1/2006 |

OTHER PUBLICATIONS

RD 480011A, Apr. 2004, Lintner.*

French Search Report issued on Nov. 27, 2008 in application No. FR 0851640.
Snyder, "Classification of the Solvent Properties of Common Liquids," *Journal of Chromatography*, vol. 92, pp. 223-230 (1974).
Abruzzo et al., "Validation of oligonucleotide microarray data using microfluidic low-density arrays: a new statistical method to normalize real-time RT-PCR data," *BioTechniques*, vol. 38, No. 5, pp. 785-792 (2005).
Al-Amoudi et al., "The molecular architecture of cadherins in native epidermal desmosomes," *Nature*, vol. 450, pp. 832-837 (Dec. 6, 2007).
Caldwell et al., "The relationship of Ki67 and involucrin expression in proliferative, pre-neoplastic and neoplastic skin," *Clinical and Experimental Dermatology*, vol. 22, pp. 11-16 (1997).
Boury-Jamot et al., "Expression and function of aquaporins in human skin: Is aquaporin-3 just a glycerol transporter," *Biochimica et Biophysica*, vol. 1758, pp. 1034-1042 (2006).
Bhawan et al., "K16 expression in uninvolved psoriatic skin: a possible marker of pre-clinical psoriasis," *Journal of Cutaneous Pathology*, vol. 31, pp. 471-476 (2004).
Benoit et al., "Elevated serum levels of calcium-binding S100 proteins A8 and A9 reflect disease activity and abnormal differentiation of keratinocytes in psoriasis," *British Journal of Dermatology*, vol. 155, pp. 62-66 (2006).
Database, Thomson Scientific London, AN 1991-003124, XP002505248 & JP 02 279618 A (Ichimaru Pharcos Inc.) Nov. 15, 1990 (Abstract).
Database, Thomson Scientific London, AN 2002-561182, XP002505273 & JP 2002 145730 (Katakura Chikkarin KK) May 22, 2002 (Abstract).
Database, Thomson Scientific London, AN 2002-580654, XP002505250 & JP 2002 205933 (Ichimaru Pharcos Inc) Jul. 23, 2002 (Abstract).

* cited by examiner

*Primary Examiner* — Patricia Leith
(74) *Attorney, Agent, or Firm* — Foley & Lardner LLP

(57) ABSTRACT

The present invention describes the use of an extract from the *Brassocattleya marcella* Koss orchid, in a cosmetic composition or for the preparation of a cosmetic composition, as a hydrating and/or anti-aging agent designed to prevent or delay the appearance of signs of intrinsic or extrinsic aging of the skin, or to delay these effects.

4 Claims, No Drawings

USE OF A *BRASSOCATTLEYA MARCELLA* KOSS ORCHID EXTRACT AS AN ACTIVE AGENT TO PREVENT OR DELAY THE APPEARANCE OF SIGNS OF CUTANEOUS AGING

The present invention describes the use of an orchid extract from the *Brassocattleya marcella* Koss species, in a cosmetic composition or for the preparation of a cosmetic composition, as a hydrating and/or anti-aging agent.

The skin is the primary barrier of the human body. It protects the organs from changes in temperature and humidity and from damage from the external environment, such as UV radiation or pollutants. It also plays an important role in homeostasis, for example, in regulating body temperature. However, excessive chemical and physical stimulation—exposure to sun, light, UV, stress and malnutrition—are harmful to the normal functions of the skin and cause aging. This extrinsic aging leads to clinical alterations such as deep wrinkles and the formation of skin that has lost its firmness, its suppleness and its elasticity. These transformations are essentially due to histopathological changes, such as an excessive modification of the elastic tissue in the upper dermis and a quantitative and qualitative degeneration of the collagen fibers.

Concomitantly, intrinsic aging, "normal" or chronobiological aging, is the consequence of planned senescence in which endogenous factors play a part. This intrinsic aging notably causes the renewal of skin cells, the keratinocytes, to slow down, which is essentially translated by the appearance of clinical changes such as the reduction of subcutaneous adipose tissue and the appearance of fine lines or wrinkles, and by histopathological changes such as an increase in the number and thickness of elastic fibers, a loss of vertical fibers of the elastic tissue membrane, and the presence of large irregular fibroblasts in the elastic tissue cells.

The present invention applies to intrinsic or physiological aging, and to extrinsic aging.

The search for new molecules or active ingredients usable in cosmetics is a necessity in order to develop efficient products to give a younger appearance to the skin, to attenuate wrinkles, to smooth the skin and to brighten the skin tone. As a result, laboratories compete in the search for more and more elaborate active ingredients. Thanks to a better knowledge of the epidermis and to the appearance of new active ingredients, anti-aging agents are becoming more and more efficient.

Several categories of anti-aging ingredients are sold today:
- antioxidants (vitamins A, C, E, trace elements, plants, and algae) fight free radicals and improve the surface of the skin and repair damage caused by pollution. More particularly, retinol, the active form of vitamin A, smoothes finer wrinkles and increases the thickness of the skin by stimulating cellular renewal,
- alpha hydroxy acids (AHA), present in citrus, grapes and sugar cane, have an exfoliating capacity that eliminates dead cells from the epidermis, and hydrates and smoothes lines to revive the clarity of the skin tone,
- new formulas also stimulate the production of collagen and elastin, promoting tissue regeneration in the same way as laser treatments, and botox-like treatments inspired by botulinum toxin to attenuate the contraction of the features.

Aging of the skin leads to numerous histopathological changes, modifying its visible beauty and quality; it may induce reduced hydration, a change in keratinocyte differentiation in the epidermis, and a slowing of keratinocyte proliferation. An interesting approach for discovering new active agents improving the structure of the epidermis is therefore to test the in vitro effects on human keratinocyte cultures.

JP2004/067549A describes the beneficial effect of orchid extracts incorporated in various compositions for preventing skin aging. This effect, observed in women of various ages, is described for the orchid species *Cattleya*.

The orchid family (Orchidaceae) comprising 25,000 species distributed into 850 genera, are among the most-heavily studied plants for the cosmetic properties of their extracts.

The cross of two natural genera, the genus *Brassavola* and the genus *Cattleya*, gives rise to plants of the sub-genus "*Brassocattleya*". Among them, the orchid *Brassocattleya marcella* Koss, also called Pink Marvel®, has been known up to now for the beauty and color of its flowers, and cultivated for its ornamental qualities. No study has precisely evaluated the properties of this genus for cosmetic purposes.

Now, in the course of their research, the inventors have shown that an orchid extract from the *Brassocattleya marcella* Koss species has an activity of primary importance for acting effectively against the biological phenomena that lead to skin aging. By means of an evaluation on normal human keratinocyte cultures, they have demonstrated the properties of a *Brassocattleya marcella* Koss extract as an active agent that can fight the effects or the appearance of signs of intrinsic and/or extrinsic skin aging.

Surprisingly, extracts containing the whole plant or parts of the *Brassocattleya marcella* Koss orchid regulate keratinocyte proliferation and differentiation of the keratinocytes of the epidermis. Cosmetic compositions containing all or part of *Brassocattleya marcella* Koss lead to obtaining finer, more regular skin, with fewer imperfections or rough spots, better light-diffusing and reflecting properties, and to improving skin hydration as well as firmness.

The first subject matter claimed by the present invention is the use of an orchid extract from the variety *Brassocattleya marcella* Koss, obtained by extraction of at least a part of said plant by means of a polar solvent or a mixture of polar solvents, in a cosmetic composition or for the preparation of a cosmetic composition, as an active hydrating agent and/or an agent for preventing or delaying the appearance of signs of intrinsic and/or extrinsic aging of the skin or for slowing these effects, in particular designed to restructure the epidermis, firm the skin and/or promote reduction or resorption of wrinkles. The plant material from which the plant extract is obtained, according to the invention, may comprise the whole plant or a part of the plant, and may, in particular, be made up of leaves, flowers, stems, roots, fruits, or mixtures formed from these different parts of the plant.

Preferentially, the part of the orchid is chosen from among the stems, the leaves and a mixture of the stems and the leaves of the orchid. Even more preferentially, the part of the orchid of the present invention is a mix of stems and leaves of the *Brassocattleya marcella* Koss orchid.

The plant or the parts of the plant selected may also be dried and/or crushed.

According to a preferred embodiment of the invention, the plant material is in the dried and crushed state.

The plant extract may be prepared by the various extraction processes known to the person skilled in the art.

Advantageously, extraction is preferably performed by contacting the selected plant material with a polar solvent or a mixture of polar solvents. According to the present invention, the expression "polar solvent" means that the solvent has a polarity index value that is greater than or equal to a value of 4. The polarity index is a quantity calculated on the basis of thermodynamic values (solubility and change of state) that indicates the degree of polarity of a molecule. For the polarity indices of solvents, one can refer to the article of L. R. SNYDER: Classification of the solvent properties of common liquids; Journal of Chromatography, 92 (1974), 223-230, which is included as a reference with the present application.

The polar solvent is advantageously chosen from among water, $C_1$-$C_4$ alcohols such as ethanol, glycols, such as ethylene glycol, glycerol, butylene glycol and propylene glycol, and their mixtures.

According to a preferred embodiment of the invention, extraction is carried out by using a water-alcohol mixture, in particular a mixture of water and ethanol, preferably a mixture of water and ethanol in a ratio of 50/50 v/v (or w/w).

According to another variant of the invention, the extraction may also be carried out by a process implementing a polar solvent in the subcritical state, said solvent advantageously being water in the subcritical state.

The extraction may also optionally comprise an additional step consisting of treating the extract in order to partially or completely decolorize it, or to purify it.

The extraction may be supplemented by a step of partial or total elimination of the extraction solvents.

In the case of partial elimination of the extraction solvents, the extract is generally concentrated until an aqueous concentration free of significant quantities of organic solvent is obtained. In the case of total elimination of these solvents, a dry residue is obtained.

Alternatively, the product from the extraction step may be freeze-dried or atomized and have the form of a powder.

The powder may be used as such in a composition, like a cosmetic composition, according to the present invention, or may be dispersed in a solvent or mixture of solvents.

Generally speaking, the product from the extraction step may be dissolved or dispersed in a solvent or a mixture of solvents, in order to be used as an active agent in the compositions of the invention.

The solvent or the mixture of solvents in which the extract is dissolved or dispersed may be identical to or different from the one used for extraction.

The extract of the invention may also be absorbed on a support advantageously chosen from among nylon powders, porous or nonporous powders and micas or any lamellar mineral substance.

In this case, the extract used is preferentially an extract in butylene glycol/water or an aqueous extract.

The anti-aging activity of the *Brassocattleya marcella* Koss orchid extract has been observed on keratinocytes. Topical application of a composition comprising a *Brassocattleya marcella* Koss orchid extract induces an improvement of the epidermal structure, by regulating both the keratinocyte proliferation and differentiation phenomena, which leads to obtaining a finer, more regular skin, with fewer imperfections and therefore diffusing and reflecting light better, as well as to obtaining a less dry, better-hydrated and firmer skin.

The composition used within the scope of the present invention is a cosmetic composition, and comprises as an active agent an extract of the *Brassocattleya marcella* Koss variety such as defined previously, and at least one excipient, such as a cosmetically-acceptable excipient. The excipient is advantageously chosen from among polymers, surfactants, rheology agents, fragrances, electrolytes, pH adjusters, antioxidants, preservatives, dyes, mother of pearl, pigments and their mixtures.

Said composition comprises an efficient quantity of orchid extract according to the present invention in order to obtain the effect sought.

The orchid extract according to the invention is advantageously present as an active agent in the composition according to a content comprised between 0.001 and 5% by weight of the composition, preferentially 0.1 to 1% by weight of the total composition.

The composition according to the invention is advantageously designed for topical application.

The composition according to the invention may be, for example, a serum, a lotion, a spray, a mousse, a solution, a powder, a pomade, a lotion, an emulsion, a tinted cream or even a hydrogel, preferably a mask, or may be in the form of a stick or a patch.

The compositions comprising the orchid extract according to the invention advantageously comprise at least one other cosmetically-acceptable active agent.

Thus, the compositions that comprise the orchid extract according to the invention may also comprise one or more other active agents that can be chosen from among substances having a skin-clarifying effect; substances having a slimming effect; substances having a hydrating effect; substances having a calming, soothing, or relaxing effect; substances that stimulate cutaneous microcirculation to improve the brightness of the skin tone, in particular for the face; substances that regulate sebum for treating oily skin; substances for cleaning or purifying the skin; substances with an antiradical effect; substances designed to attenuate or delay the effects of skin aging, in particular the formation of wrinkles, by an activity seeking to promote structural maintenance of the skin and/or limit the degradation of the extracellular matrix of the superficial layers of the dermis and the epidermis and/or to obtain a protective, corrective, or restructuring effect for the skin; substances having an anti-inflammatory effect.

In a particularly preferred manner, the orchid extract of the invention is combined with active agents chosen from among:
  purified molecules or extracts promoting cellular renewal, such as vitamin A, retinol or retinol esters; alpha- or beta-hydroxy acids such as fruit acids, malic, glycolic, citric acids, salicylic acid or its esters, gentisic acid or its esters, in particular tocopherol gentisate,
  molecules or extracts stimulating skin firmness, peptide collagen stimulators, extracts of de *Centella asiatica* alone or in combination, madecassic acid, asiatic acid, madecassoside, oat extracts, soy peptides, *Potentilla erecta* extract, *Siegesbeckia orientalis* extract, ginsenosides or notoginsenosides, in particular Rb1,
  molecules or extracts regulating the differentiation of the epidermis, including ecdysteroids, ecdysterone, turkesterone or calcium derivatives, vitamin D precursors,
  metalloprotease inhibitors, in particular MMP1, 2 and 9 inhibitors, such as *Ruscus asculeatus* extract, or soy peptides, or flavonoids such as quercetin, kaempferol, apigenin, wogonin, or plant extracts containing them,
  elastase inhibitors such as plant extracts of *Aspergillus fumigatus, Momordica charantia, Cucurbita maxima,*
  substances capable of stimulating dermatopontin synthesis, such as an amber extract,
  molecules or extracts from astringent plants tightening the pores, such as witch hazel extracts,
  sunscreens protecting from UVA and UVB radiation, such as benzophenone-4 butyl methoxydibenzoylmethane, ethylhexyl methoxycinnamate, octocrylene, ethylhexyl salicylate, phenylbenzimidazole sulfonic acid, homosalate, alone or in combination with titanium oxides.
  plant molecules or extracts recognized has having effects on pigmentation, such as kojic acid, kushenol B, licorice root extracts, arbutine, calcium panteteheine sulfonate, boldine, diacetyl boldine, vitamin C derivatives, lily extracts, notably *Lilium candidum*, in particular from the bulb, or even soy extracts, antiradical or anti-inflammatory molecules, extracts of *Artemisia capillaris*, extracts of *Sanguisorba officinalis*, resveratrol and its derivatives, turmeric or curcumin or tetrahydrocurcumin, grapeseed polyphenols, vitamin E and its derivatives, in particular its phosphate derivatives, ergothioneine or its derivatives, idebenone, molecules or extracts promoting hyaluronic acid synthesis at the epidermal and dermal level or glycosaminoglycans to give superbly hydrated and firm skin, in particular an extract of *Eriobotrya*, notably an extract of *Eriobotrya japonica*, or small fragments of hyaluronic acid, surface hydrating molecules such as natural glycols or polyols, natural or synthetic ceramides, spring or mineral waters.

Advantageously, according to the present invention, the cosmetic composition comprises, in addition to the orchid extract according to the invention, at least one other active agent chosen among the group made up of boldine or one of its cosmetically-acceptable derivatives, in particular diacetyl boldine, D-xylose, *Eriobotrya* extract, notably *Eriobotrya japonica* extract, or hyaluronic acid fragments, and their mixtures.

According to a particularly preferred embodiment of the invention, the composition also comprises boldine or one of its cosmetically-acceptable derivatives, in particular diacetyl boldine, in addition to the orchid extract according to the invention.

According to another preferred embodiment of the invention, the composition comprises D-xylose in addition to the orchid extract according to the invention.

According to another preferred embodiment of the invention, the composition comprises an *Eriobotrya* extract in addition to the orchid extract according to the invention, notably an *Eriobotrya japonica* extract, hyaluronic acid or hyaluronic acid fragments.

According to another preferred embodiment of the invention, the composition comprises molecules or extracts stimulating skin firmness in addition to the orchid extract according to the invention, notably collagen stimulators peptides, *Centella asiatica* extracts, alone or in combination, madecassic acid, asiatic acid, madecassoside, oat extracts, soy peptides, *Potentilla erecta* extracts, notoginsenosides, and Rb1 in particular, or their mixtures.

According to another preferred embodiment of the invention, the composition comprises molecules regulating the differentiation of the epidermis in addition to the orchid extract according to the invention, such as ecdysteroids, ecdysterone, turkesterone, calcium derivatives, or their mixtures.

According to another preferred embodiment of the invention, the composition comprises metalloprotease inhibitors in addition to the orchid extract according to the invention, in particular MMP1, 2 and 9 inhibitors, such as a *Ruscus asculeatus* extract, or soy peptides, or flavonoids such as apigenin, wogonin, or plant extracts containing them, or their mixtures.

The present invention also pertains to a method of cosmetic care seeking to hydrate the skin and/or to prevent or delay the appearance of the effects of intrinsic and/or extrinsic aging of the skin, or to slow down these effects, said method being characterized in that it comprises the application onto at least part of the skin of the body or face of a cosmetic composition containing an orchid extract from the species *Brassocattleya marcella* Koss such as defined previously as an active agent, typically obtained by extraction of at least part of said plant by means of a polar solvent or a mix of polar solvents.

The examples below illustrate the invention without restricting the scope.

EXAMPLE 1

Examples of Extracts Made from the *Brassocattleya marcella* Koss Orchid

Extract 1

An extract from the stem and leaves with 50% butylene glycol/water is made by 24 h of maceration, then filtered, cooled for 18 h, and filtered; the filtrate is collected and tested. For example, 50 g of fresh stems and leaves are placed in the macerator for 48 hours with gentle stirring at ambient temperature in a 50/50 mixture of butylene glycol/water, then the mixture is filtered, and the filtrate is recovered and kept at 4° C. for 24 hours. The filtrate is filtered then recovered to test its anti-aging activity.

Extract 2

An extract of the aerial parts (stem and leaves) of the plant is extracted by a water-alcohol mixture preferentially made up of ethanol/water (70/30 v/v) at 70° C., at ambient temperature. The solution obtained after filtration is concentrated to 20% of the initial volume in the rotary evaporator under vacuum and then refiltered. The solution obtained is an extract usable in cosmetics in compositions according to the invention, such as cosmetic compositions according to Example 3.

Extract 3

An extract of the leaves and stems is hot-extracted by a water/ethanol mixture (95/5 v/v) for minutes, and left to cool. The solution is then filtered and freeze-dried. The freeze-dried product obtained is taken up in butylene glycol and titrated at 1% by dry weight. This extract is usable in cosmetics in compositions according to the invention, such as cosmetic compositions according to Example 3.

EXAMPLE 2

Evaluation of the Effect of the Extract containing *Brassocattleya marcella* Koss on Normal Human Keratinocytes Keratinocyte extracts from samples of normal human skin obtained from plastic surgery. These cells are cultivated in a K-SFM medium supplemented with pituitary extract and EGF.

The cells are treated for 24 hours under different conditions:

Extract 1 of example 1, 1% *Brassocattleya marcella* Koss (v/v)

1% (butylene glycol) solvent=control.

After 24 hours of incubation under the non-cytotoxic conditions described above, the culture media are eliminated then the total RNA is extracted. To do this, the cells are placed on a bed of ice without pre-rinsing. Under a chemical hood, these cells are mechanically detached and lysed in 1 mL of RNA-plus reagent (gbiogene) then everything is recovered in an Eppendorf tube. The total RNA extracted is then assayed by means of a bioanalyzer (Agilent 2100) and the RNA 6000 nanolabchip kit (Agilent). Finally, a reverse-transcription step is performed on the total RNA by means of the Applied Biosystem High Capacity cDNA archive kit in order to obtain complementary DNA.

The influence of the various treatments on the modulation of various genes of interest is evaluated by the Taqman Low Density Array technology (TLDA from Applied Biosystem), according to the protocol below:

50 µL of each of the cDNAs are mixed with 50 µL Universal Master Mix buffer, the 100 µL obtained are deposited on a "micro-fluidic DNA chip". The chip is centrifuged twice at 1200 g, then the line of cDNA deposition is cut out, and introduced into the TLDA HT 7900 apparatus (Applied Biosystem). The samples present loaded onto the chip are then subjected to a succession of PCR reactions.

The results obtained by means of this technology permit quantitatively showing the changes in the expression profile of specific genes of the cell type studied (for more detail, see L. V. Abruzzo et al, Biotechniques, 2005, 38, 785-792).

The percentages of stimulation or inhibition observed are summarized in the table below.

| Accession Number | Gene Name | Abbreviation | Modulation (in % with regard to the control) |
|---|---|---|---|
| NM_004925 | Aquaporin-3 | AQP3 | 13.2 |
| NM_004360 | Epithelial-Cadherin precursor | E-Cadherin (CDH 1) | 30.5 |
| NM_005557 | Cytokeratin 16 | KRT16 | −12.41 |
| NM_002417 | Antigen Ki67 | Ki67 (MK167) | 53.1 |
| NM_002964 | S100 calcium binding protein A8 (calgranulin A) | S100A8 | 15.16 |

The *Brassocattleya* extract:
  Stimulates the gene coding for AQP3, aquaporin-3, a protein involved in skin hydration (see: "Expression and function of aquaporins in human skin: Is aquaporin-3 just a glycerol transporter?", Boury-Jamot M et al, BBA 2006, 1758(8):1034-42).
  Stimulates the gene coding for E-cadherins, proteins responsible for cellular cohesion between cells (see: "The molecular architecture of cadherins in native epidermal desmosomes", Al-Amoudi A et al, Nature 2007, 450(7171): 832-37),
  Stimulates the gene coding for Ki67, a marker of normal cellular proliferation (see: "The relationship of Ki67 and involucrin expression in proliferative, pre-neoplastic and neoplastic skin", Caldwell C J et al, Clin Exp Dermatol. 1997 January; 22(1):11-6).
  Suppresses the K16 gene, the gene for epidermal hyperproliferation (see: "K16 expression in uninvolved psoriatic skin: a possible marker of pre-clinical psoriasis", Bhawan J et al, J Cutan Pathol. 2004 August; 31(7):471-6).
  Suppresses the gene coding for calgranulin A, calcium binding protein that is involved in epidermal differentiation, and that is overexpressed in disorders like psoriasis (see: "Elevated serum levels of calcium-binding S100 proteins A8 and A9 reflect disease activity and abnormal differentiation of keratinocytes in psoriasis", Benoit S et al, Br J. Dermatol. 2006 July; 155(1):62-6.).

All the targets modulated by a *Brassocattleya marcella* Koss extract are of first importance for effectively fighting the biological phenomena that lead to skin aging and noticeable changes in one's appearance with age. The activity of the composition containing *Brassocattleya marcella* Koss, observed on keratinocytes, induces an improvement of the epidermal structure by regulating both the keratinocyte proliferation and differentiation phenomena, which will lead to obtaining a finer, more regular skin, with fewer imperfections and therefore diffusing and reflecting light better.

EXAMPLE 3

Anti-Aging Formulations Containing the *Brassocattleya marcella* Koss Orchid Extract Anti-Aging Emulsion Comprising:

| | |
|---|---|
| Extract 3 of example 1, *Brassocattleya marcella* Koss: | 0.5% |
| Tetrahydrocurcuminoids: | 0.1% |
| Lactic acid: | 2% |
| Pentylene glycol: | 3% |
| Glycerin: | 2% |
| ethylhexyl methoxycinnamate: | 5% |
| Scented excipient qsp: | 100% |

Anti-Wrinkle Foundation:

| | |
|---|---|
| Extract 3 according to example 1, *Brassocattleya marcella* Koss: | 0.1% |
| ergothioneine: | 0.05% |
| hyaluronic acid: | 2% |
| pigments: | 3% |
| shea butter: | 0.8% |
| UV screens: | 5% |
| micronized titanium oxide: | 2% |
| excipient qsp | 100% |

Firming Anti-Wrinkle Serum:

| | |
|---|---|
| Extract 2 according to example 1, *Brassocattleya marcella* Koss: | 0.3% |
| Extract of *Eriobotrya japonica*: | 0.2% |
| D xylose: | 0.1% |
| Wheat ceramides: | 0.2% |
| Digalactosyl diglyceride: | 0.15% |
| Amber extract: | 1% |
| Retinyl palmitate: | 1500 UI |
| Oxybenzon: | 3% |
| Excipient qsp | 100% |

The invention claimed is:

1. A method of cosmetic care for hydrating the skin and/or preventing or delaying the appearance of the effects of intrinsic and/or extrinsic aging of the skin, or to slow down these effects, wherein said method comprises the application onto at least part of the skin of a body or a face, a cosmetic composition containing, as active agent, an orchid extract from *Brassocattleya marcella* Koss wherein said composition comprises:
  (a) *Brassocattleya marcella* Koss extract, tetrahydrocurcuminoids, lactic acid, pentylene glycol, glycerin, and ethylhexyl methoxycinnamate; or
  (b) *Brassocattleya marcella* Koss extract ergothioneine, hyaluronic acid, pigments, shea butter, UV screens, and micronized titanium oxide, or
  (c) *Brassocattleya marcella* Koss extract, *Eriobotrya japonica* extract, D xylose, wheat ceramides, digalactosyl diglyceride, amber extract, 1500 UI retinyl palmitate, and oxybenzon.

2. The method of claim 1, wherein the prevention or delay of the appearance of the effects of intrinsic and/or extrinsic aging of the skin, or the slowing down of these effects comprises the restructuration of the epidermis, the firming of the skin, and/or the promotion of the attenuation of wrinkles.

3. The method of claim 1, wherein said extract is present in the cosmetic composition between 0.001 and 5% by weight of the composition.

4. The method of claim 3, wherein said extract is present in the cosmetic composition at 0.1 to 1% by weight of the composition.

* * * * *